Figure 1:
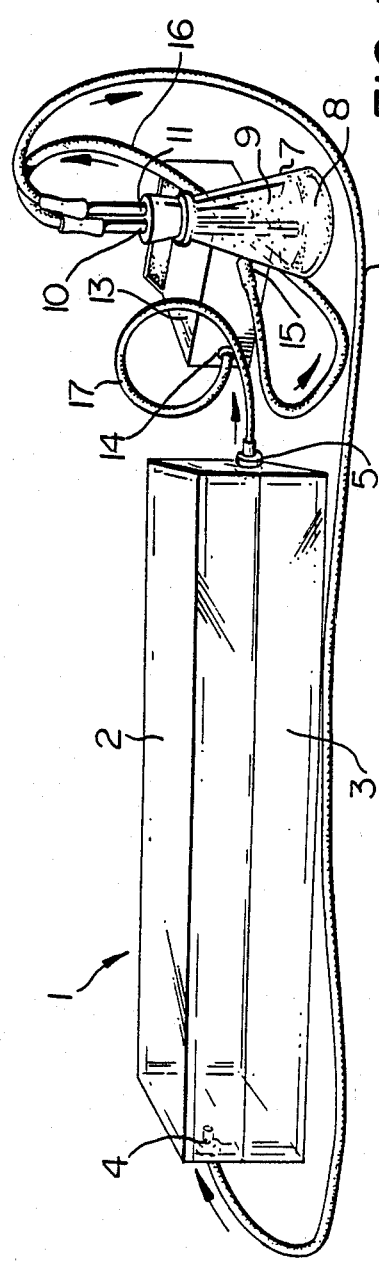

United States Patent [19]

Bourdon

[11] 4,297,383

[45] Oct. 27, 1981

[54] APPARATUS AND METHOD FOR OBTAINING FINGERPRINTS

[76] Inventor: Louis P. Bourdon, R.R. #3, Hwy. 17, East Twin Lakes, North Bay, Ontario, Canada, P1B 8G4

[21] Appl. No.: 186,624

[22] Filed: Sep. 12, 1980

[30] Foreign Application Priority Data

Jul. 15, 1980 [CA] Canada .................................. 356161

[51] Int. Cl.³ .......................... A61B 5/10; C23C 13/06
[52] U.S. Cl. ....................................... 427/1; 118/31.5; 118/719; 118/733; 427/145; 427/255.4; 427/345
[58] Field of Search ................ 427/1, 255.4, 145, 345; 118/31.5, 719, 733

[56] References Cited

U.S. PATENT DOCUMENTS 3,546,003 12/1970 Reid et al. ........................ 427/255.4

FOREIGN PATENT DOCUMENTS

| 749617 | 1/1967 | Canada. |
| 806942 | 2/1969 | Canada. |
| 865374 | 3/1971 | Canada. |
| 907203 | 8/1972 | Canada. |
| 973358 | 8/1975 | Canada. |
| 1001413 | 12/1976 | Canada. |
| 1428025 | 3/1973 | United Kingdom ............... 118/31.5 |

Primary Examiner—Ronald H. Smith
Assistant Examiner—Janyce A. Bell
Attorney, Agent, or Firm—Cushman, Darby & Cushman

[57] ABSTRACT

This invention relates to an apparatus and method for developing latent fingerprints on an object by fuming said object with the vapors of the chemical cyanoacrylate. Apparatus is disclosed comprising a first chamber to contain the object and to close to form an air tight seal, a second chamber to contain the chemical pool and vapors thereof and a pump system. The method involves pumping the vapors from the second chamber into the first chamber to develop the latent fingerprints on the object to be tested.

8 Claims, 2 Drawing Figures

U.S. Patent  Oct. 27, 1981  4,297,383

APPARATUS AND METHOD FOR OBTAINING FINGERPRINTS

This invention relates to apparatus and method for developing latent fingerprints on an object. More particularly, this invention discloses method and apparatus for fuming an object suspected of containing fingerprints with the vapors of the chemical cyanoacrylate.

In the prior art, a number of methods of developing fingerprints have been disclosed. The purpose of most of these methods is to permit fingerprints to be visually displayed on an object without disturbing the fingerprint by means of the development procedure. Many of the prior art methods require that the fingerprints be brushed with a powder or soaked in a solution or otherwise dealt with in a manner which might smudge or harm the latent fingerprints to be developed. The present invention provides an improved method of developing latent fingerprints which does not require that the object be dipped, soaked, brushed or touched in any fashion.

Essentially, this invention comprises a method for developing latent fingerprints on an object comprising placing the object to be tested in a first chamber, sealing said first chamber, exposing the interior of said first chamber and the object therein to the vapors of the chemical cyanoacrylate until said latent fingerprints become visible.

More particularly, this invention comprises a method as described above in which the vapors of the chemical cyanoacrylate are pumped into said first chamber from a second chamber containing a pool of the chemical cyanoacrylate and the vapors thereof by means of a pump and suitable tubing.

It will be appreciated by those skilled in the art that the method may be operated either by exhausting said first chamber to the atmosphere or by recirculating the air and fumes thereof through the system. In the recirculation mode, the air exhausted from said first chamber may be recirculated through said pumping means to said second chamber containing a pool of and the vapors of the chemical cyanoacrylate. The air and the vapors mix and the mixture continues on into said first chamber and recycles again.

The apparatus of this invention essentially comprises a means for developing latent fingerprints on an object comprising a first chamber being adapted to open to receive an object to be tested for fingerprints and to close to form an air tight seal, said first chamber having an inlet and an outlet, a second chamber adapted to contain a pool of and the vapors of the chemical cyanoacrylate, said second chamber having an inlet and an outlet, the outlet of said second chamber being connected by suitable tubing to the inlet of said first chamber, a recirculating pump means having an intake and an exhaust, said exhaust being connected to the inlet of said second chamber by suitable tubing, said intake being connected to the outlet of said first chamber by suitable tubing, said recirculating pump means being adapted to circulate the vapors and air between said first and second chambers so as to expose said latent fingerprints to said vapors thereby developing visible fingerprints.

The foregoing apparatus may be adapted so that the recirculating pump means is driven by a variable speed motor which allows an operator to control the rate of exposure of fingerprints to the vapors.

The foregoing apparatus may have a first chamber comprising a plexiglass container having two halves, top and bottom, which open and close in a sealed relationship against each other.

The first chamber may have an insert means which may be placed between the top and bottom halves of the plexiglass container so as to increase the size of the first chamber.

In the figures which illustrate the preferred embodiments of the apparatus of this invention, FIG. 1 is a sketch of a recirculating fuming system.

Figure 2:
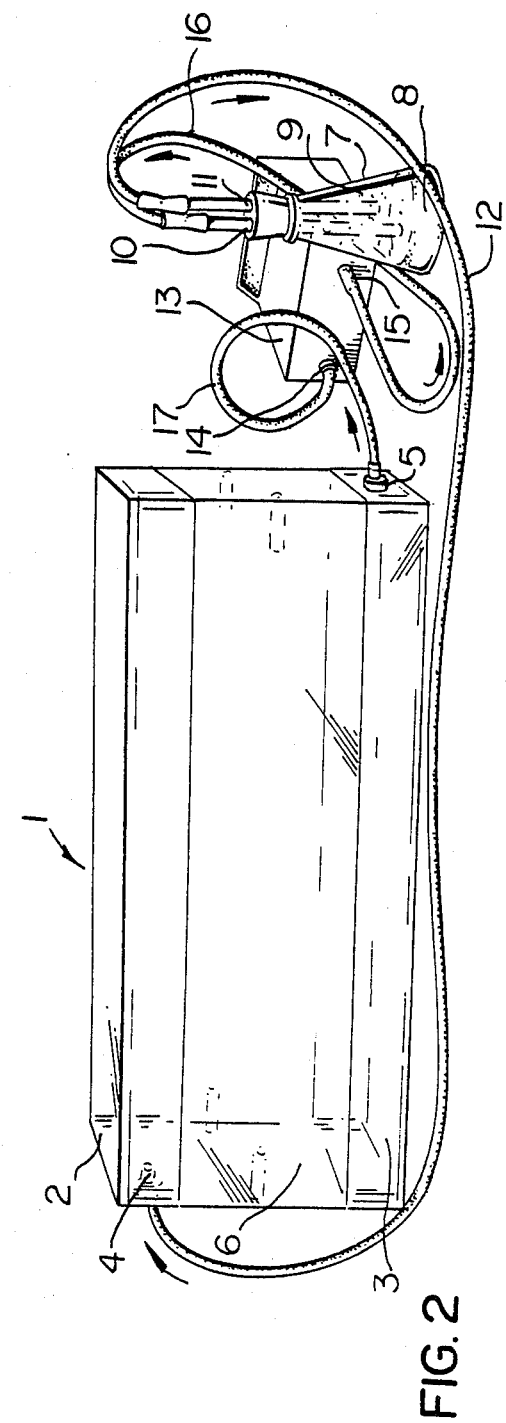

FIG. 2 illustrates the apparatus of FIG. 1 including an insert means comprising a removable center section.

In the figures which illustrate this invention, like numerals are used to indicate like elements.

The preferred embodiments of this apparatus are shown in FIGS. 1 and 2 and comprise a first rectangular box-like chamber 1 having top and bottom halves, 2 and 3 respectively, an inlet 4 and an outlet 5. The first chamber 1 is used to contain the object to be tested for fingerprints; the object may be inserted into the chamber 1 simply by separating the top and bottom halves 2 and 3, inserting the object and then closing and sealing the halves together. As illustrated in FIG. 2, if the object is larger than might be accommodated by said first chamber top and bottom halves 2 and 3, an insert means comprising a removable center section 6 may be inserted in sealed relationship between said top and bottom halves 2 and 3 to increase the size of the chamber 1 to accommodate the object.

A second chamber 7 contains a pool of the chemical cyanoacrylate 8 and vapors thereof 9. Said second chamber 7 has an inlet 10 and an outlet 11. The outlet 11 of said second chamber 7 being connected to the inlet 4 of said first chamber 1 by means of suitable tubing 12. A recirculating pump 13 having intake 14 and exhaust 15 is used to recirculate air and vapors between the first and second chambers. The exhaust 15 of the recirculating pump 13 is connected to the inlet 10 of the second chamber 7 by means of suitable tubing 16. The intake 14 of said recirculating pump 13 is connected to the outlet 5 of the first chamber 1 by means of suitable tubing 17.

In operation, the object to be tested for fingerprints is placed in the first chamber. The second chamber is partially filled with a pool of the chemical cyanoacrylate and the vapors are allowed to fill the second chamber. At this point, the recirculating pump may be turned on to pump vapors and air around the system so as to diffuse the vapors throughout the first chamber thereby exposing the object to be tested therein to such vapors. Continuous exposure over a period of time will have the effect of developing latent fingerprints on most objects.

It will be appreciated by those skilled in the art that the development of the fingerprints by means of this fuming apparatus may be accelerated by increasing the density of the fumes. It will also be appreciated that the time required to fully develop such fingerprints will depend upon the state of the fingerprint itself and the nature of the object to be tested. Generally, if a fingerprint is indicated fuming may be repeated until the necessary results are achieved. It has been found that apparatus of the above invention will develop visual fingerprints on very difficult surfaces such as plastics, plastic bags, aluminum, silverware and steel in anywhere from 20 minutes to 24 hours, depending upon the material and the state of the fingerprint.

It will be appreciated by those skilled in the art that the features of the above described apparatus and method may be modified without departing from the essential characteristics of the principle of this invention.

The embodiments of the invention in which an exclusive property or privilege is claimed are defined as follows:

1. An apparatus for developing latent fingerprints on an object comprising a first chamber adapted to contain an object being tested for fingerprints, and to close to form an air tight seal, said first chamber having an inlet and an outlet, a second chamber adapted to contain a pool of and the vapors of the chemical cyanoacrylate, said second chamber having an inlet and an outlet, the outlet of said second chamber being connected by suitable tubing to the inlet of said first chamber, a recirculating pump means having an intake and an exhaust, said exhaust being connected to the inlet of said second chamber, said intake being connected to the outlet of said first chamber by suitable tubing, said recirculating pump means being adapted to circulate the vapors and air between said first and second chambers so as to expose said latent fingerprints to said vapors thereby developing visible fingerprints.

2. The apparatus of claim 1 in which said recirculating pump means is driven by a variable speed motor which allows an operator to control the rate of exposure of fingerprints to the vapors.

3. The apparatus of claim 1 in which the first chamber comprises a plexiglass container having two halves, top and bottom, which open and close in a sealed relationship against each other.

4. The apparatus of claim 3 additionally comprising an insert means being adapted to be inserted in sealed relationship between the top and bottom halves of the plexiglass container so as to increase the size of said first chamber.

5. The apparatus of claims 1, 3 or 4 in which said first chamber comprises a rectangular box.

6. A method for developing latent fingerprints on an object comprising placing the object to be tested in a first chamber, sealing said first chamber, exposing the interior of said first chamber and the object therein to the vapors of the chemical cyanoacrylate until said latent fingerprints become visible.

7. The method of claim 6 in which the vapors of the chemical cyanoacrylate are pumped into said first chamber from a second chamber containing a pool of the chemical cyanoacrylate and the vapors thereof by means of a pump and suitable tubing.

8. The method of claim 7 in which the air exhausted from said first chamber is recirculated through said pumping means to said second chamber containing a pool of and the vapors of the chemical cyanoacrylate and back into said first chamber mixed with said vapors.

* * * * *